(12) United States Patent
Harada et al.

(10) Patent No.: US 10,420,518 B2
(45) Date of Patent: Sep. 24, 2019

(54) X-RAY COMPUTED TOMOGRAPHY IMAGING APPARATUS AND X-RAY TUBE APPARATUS

(71) Applicant: Toshiba Medical Systems Corporation, Otawara-shi (JP)

(72) Inventors: Sanae Harada, Nasushiobara (JP); Hiroaki Miyazaki, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 195 days.

(21) Appl. No.: 15/277,144

(22) Filed: Sep. 27, 2016

(65) Prior Publication Data

US 2017/0092457 A1    Mar. 30, 2017

(30) Foreign Application Priority Data

Sep. 30, 2015  (JP) .................. 2015-194385
Sep. 13, 2016  (JP) .................. 2016-178585

(51) Int. Cl.
| A61B 6/03 | (2006.01) |
| A61B 6/00 | (2006.01) |
| H05G 1/46 | (2006.01) |
| H05G 1/56 | (2006.01) |

(52) U.S. Cl.
CPC .............. *A61B 6/032* (2013.01); *H05G 1/46* (2013.01); *H05G 1/56* (2013.01); *A61B 6/405* (2013.01); *A61B 6/4488* (2013.01)

(58) Field of Classification Search
CPC ....... A61B 6/032; A61B 6/405; A61B 6/4488; H05G 1/46; H05G 1/56
See application file for complete search history.

(56) References Cited

U.S. PATENT DOCUMENTS

| 4,654,797 A * | 3/1987 | Fujita | ................. G06T 11/006 |
| | | | 378/14 |
| 4,995,069 A * | 2/1991 | Tanaka | ................. A61B 6/035 |
| | | | 378/101 |
| 6,778,633 B1 * | 8/2004 | Loxley | ................. H01J 35/14 |
| | | | 378/113 |
| 7,016,468 B1 * | 3/2006 | Krema | ................. H05G 1/34 |
| | | | 378/101 |

(Continued)

FOREIGN PATENT DOCUMENTS

| JP | 2002-319359 | 10/2002 |
| JP | 2004-296242 | 10/2004 |

(Continued)

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray computed tomography imaging apparatus includes an X-ray tube, an X-ray detector, and control circuitry. The X-ray tube includes a cathode configured to generate thermoelectrons, an anode configured to generate X-rays upon receiving the thermoelectrons from the cathode, and a regulator configured to apply an electric field or a magnetic field to focus or bias the thermoelectrons from the cathode. The X-ray detector detects the X-rays generated by the anode. The control circuitry controls the regulator to switch at least one of the size and position of the focus of the thermoelectrons from the cathode on the anode between scan and warm-up.

12 Claims, 8 Drawing Sheets

(56) References Cited

U.S. PATENT DOCUMENTS

| | | | |
|---|---|---|---|
| 2011/0280363 A1 | 11/2011 | Zou et al. | |
| 2014/0355736 A1 | 12/2014 | Harada | |
| 2015/0063530 A1* | 3/2015 | Liu ....................... | A61B 6/107 |
| | | | 378/16 |

FOREIGN PATENT DOCUMENTS

| | | |
|---|---|---|
| JP | 2011-238614 | 11/2011 |
| JP | 2014-61287 | 4/2014 |

* cited by examiner

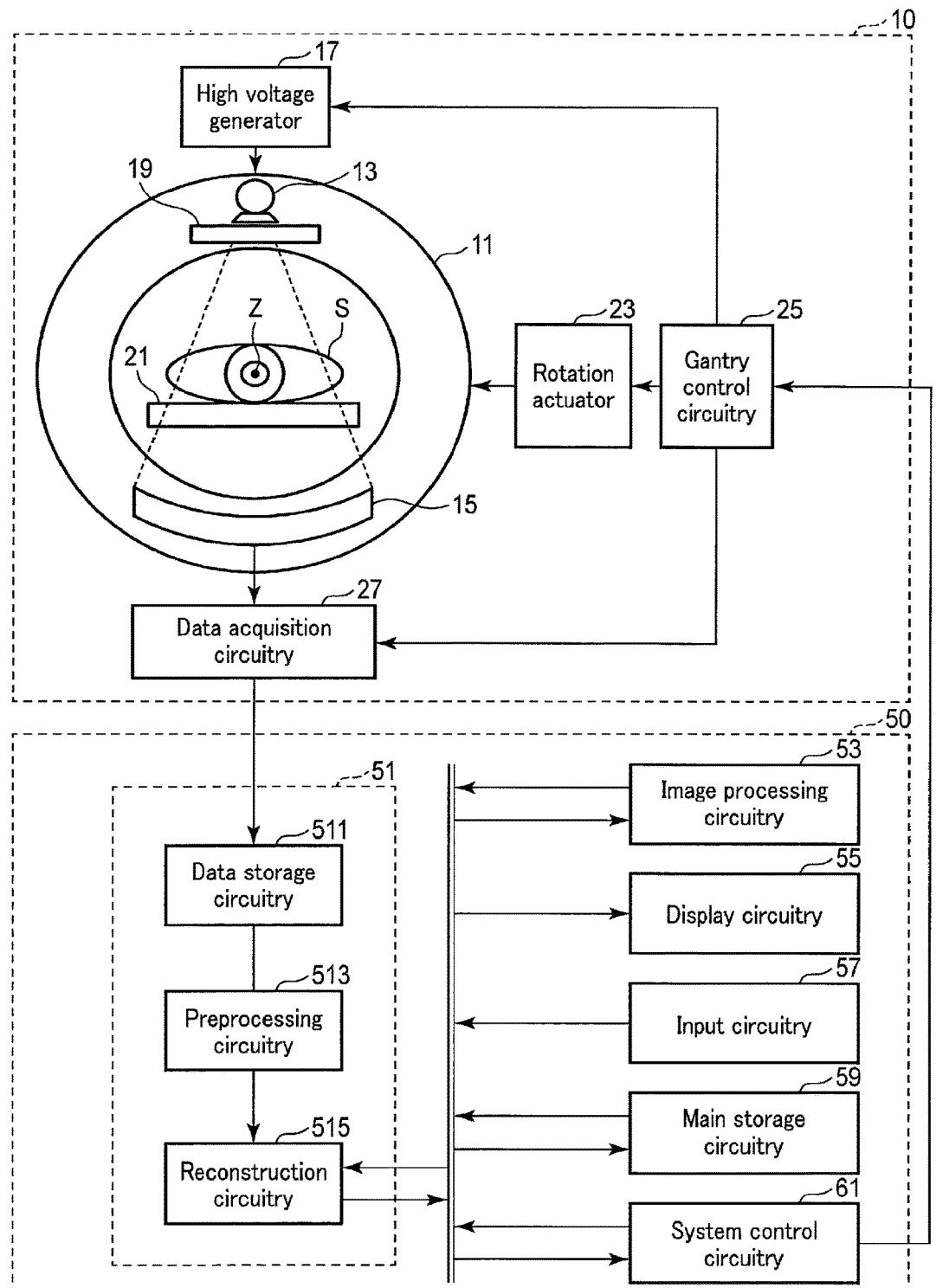
F I G. 1

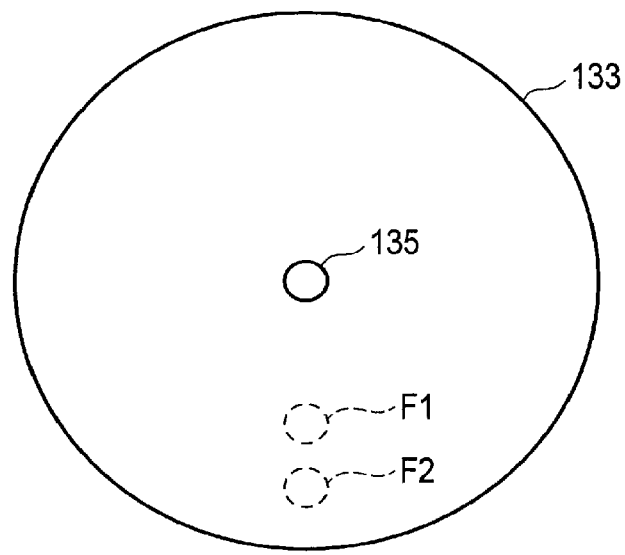
F I G. 5
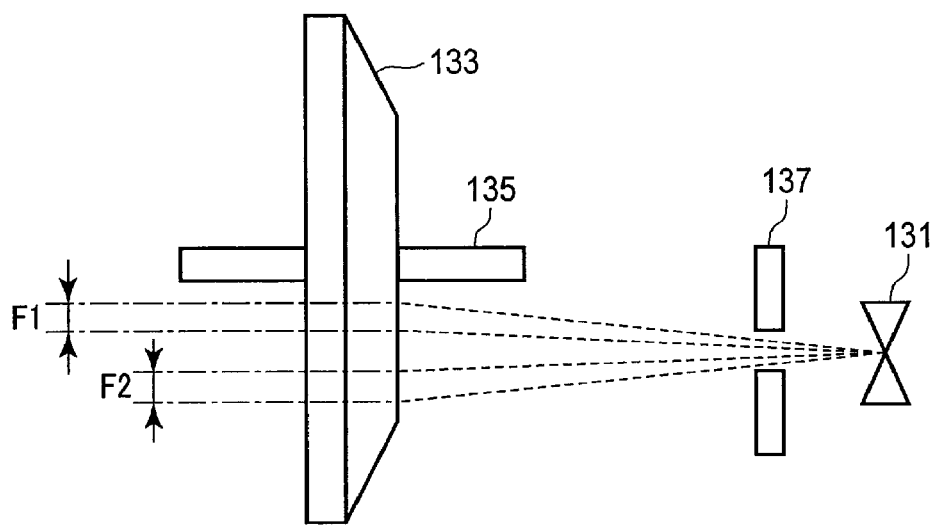
F I G. 6

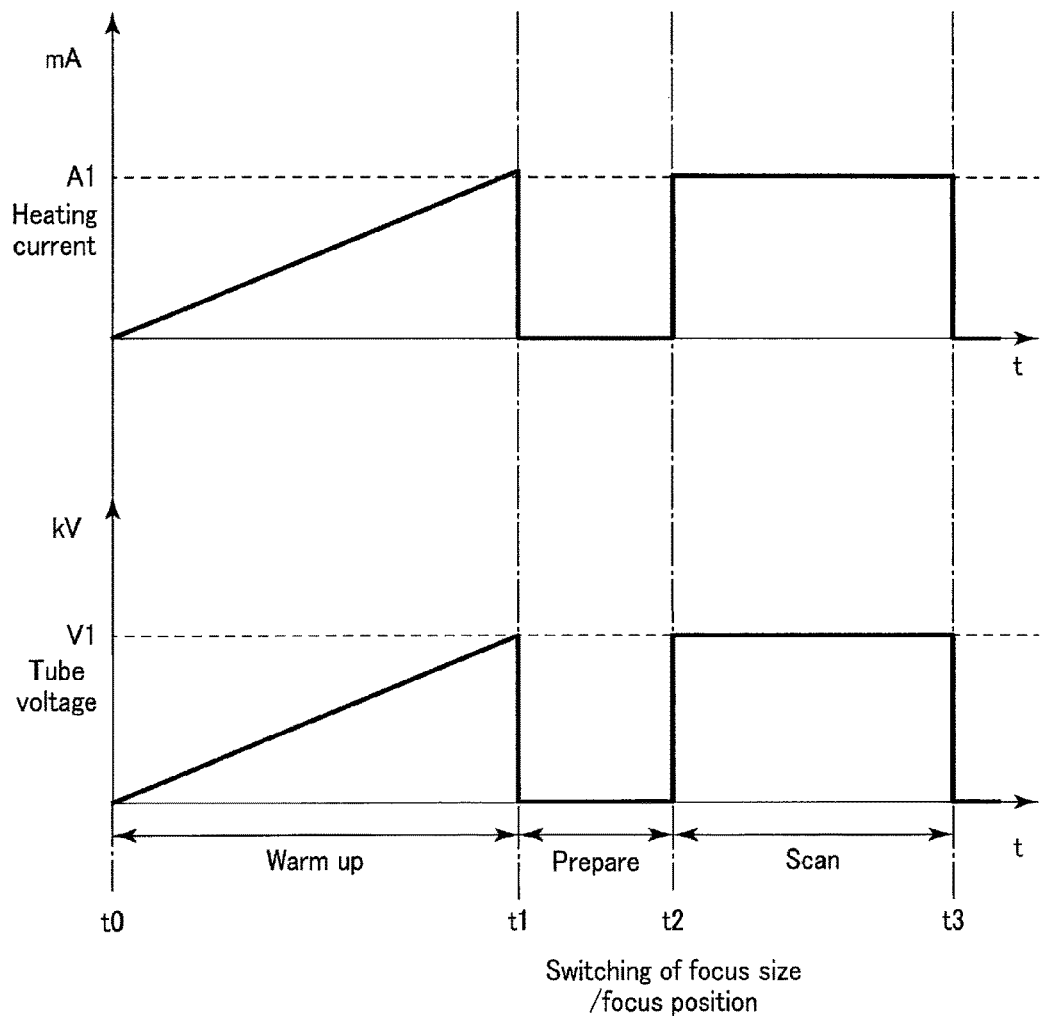
F I G. 7

US 10,420,518 B2

X-RAY COMPUTED TOMOGRAPHY IMAGING APPARATUS AND X-RAY TUBE APPARATUS

CROSS-REFERENCE TO RELATED APPLICATIONS

This application is based upon and claims the benefit of priority from the prior Japanese Patent Application No. 2015-194385, filed Sep. 30, 2015 and the prior Japanese Patent Application No. 2016-178585, filed Sep. 13, 2016, the entire contents of all of which are incorporated herein by reference.

FIELD

Embodiments described herein relate generally to an X-ray computed tomography imaging apparatus and an X-ray tube apparatus.

BACKGROUND

An X-ray computed tomography imaging apparatus includes an X-ray tube that generates X-rays. Before scan, to maintain the cleanliness in the X-ray tube or raise the temperature of components such as a rotating anode in the X-ray tube to a predetermined value or more, the X-ray tube is warmed up by applying a high voltage and supplying a filament heating current.

Since the warm-up is performed using a cathode used for scan, the life of the cathode may be shortened by the application purpose other than scan. In addition, since the size of a focus is fixed, the surface of the anode may roughen.

BRIEF DESCRIPTION OF THE DRAWING

FIG. 1 is a view showing the arrangement of an X-ray computed tomography imaging apparatus according to the embodiment;

FIG. 5 is a front view of the anode on which a focus position for scan and a focus position for warm-up according to other Example 1 are shown;

FIG. 6 is a side view of the anode on which the focus position for scan and the focus position for warm-up according to other Example 1 are shown;

FIG. 7 is a timing chart of a heating current and a tube voltage concerning switching of the focus size according to Example 1;

DETAILED DESCRIPTION

Figure 2:
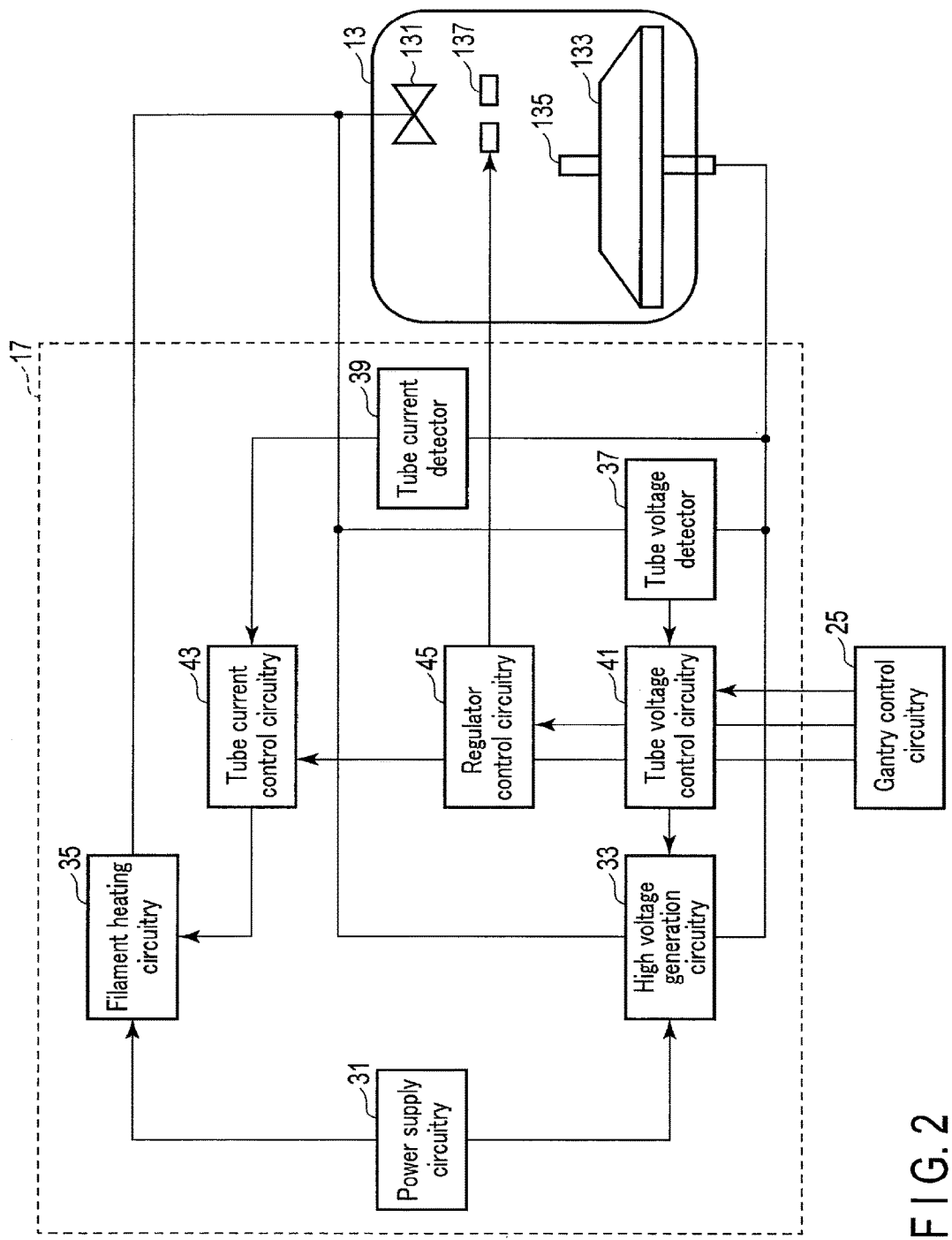
FIG. 2 is a view showing the arrangement of an X-ray tube and a high voltage generator according to Example 1.

An X-ray computed tomography imaging apparatus according to this embodiment includes an X-ray tube, an X-ray detector, data acquisition circuitry, image generation circuitry, and control circuitry. The X-ray tube includes a cathode configured to generate thermoelectrons, an anode configured to generate X-rays upon receiving the thermoelectrons from the cathode, and a regulator configured to apply an electric field or a magnetic field to focus or bias the thermoelectrons from the cathode. The X-ray detector detects the X-rays generated by the anode. The data acquisition circuitry acquires data corresponding to the X-rays detected by the X-ray detector. The image generation circuitry generates an image based on the acquired data. The control circuitry controls the regulator to switch at least one of the size and position of the focus of the thermoelectrons from the cathode on the anode between scan and warm-up.

The X-ray computed tomography imaging apparatus and an X-ray tube apparatus according to this embodiment will now be described with reference to the accompanying drawing.

FIG. 1 is a view showing the arrangement of the X-ray computed tomography imaging apparatus according to this embodiment. As shown in FIG. 1, the X-ray computed tomography imaging apparatus according to this embodiment includes a gantry 10 and a console 50. For example, the gantry 10 is placed in a CT examination room, and the console 50 is placed in a control room adjacent to the CT examination room. The gantry 10 and the console 50 are connected wirelessly or via a cable to be communicable with each other. The gantry 10 is a scanning apparatus having an arrangement for performing X-ray computed tomography imaging (to be referred to as X-ray CT imaging hereinafter) of a subject S. The console 50 is a computer that controls the gantry 10.

As shown in FIG. 1, the gantry 10 includes an almost cylindrical rotation frame 11 with a bore that forms a field of view. As shown in FIG. 1, an X-ray tube 13 and an X-ray detector 15 which are arranged to face each other via the bore are attached to the rotation frame 11. The rotation frame 11 is a metal frame made of a metal such as aluminum into an annular shape. The X-ray tube 13 and the X-ray detector 15 may be, for example, fitted in concave portions formed in the rotation frame 11 or fastened using fasteners such as a screw. More specifically, the gantry 10 has a main frame (not shown) made of a metal such as aluminum. The rotation frame 11 is supported by the main frame via a bearing and the like to be rotatable about a center axis Z. An slip ring (not shown) is provided on the contact portion of the main frame to the rotation frame 11. A conductive brush (not shown) is attached to the contact portion of the main frame to be in slidable contact with the slip ring. Power from a power supply unit (not shown) stored in the gantry 10 is supplied via the slip ring and the brush to various kinds of devices such as the X-ray detector 15 and a high voltage generator 17 mounted on the rotation frame 11.

The X-ray tube 13 is connected to the high voltage generator 17. The high voltage generator 17 is attached to, for example, the rotation frame 11. The high voltage generator 17 generates a high voltage to be applied to the X-ray tube 13 from the power supplied from the power supply unit (not shown) of the gantry via the slip ring and the brush and supplies a filament heating current under the control of gantry control circuitry 25. The high voltage generator 17 and the X-ray tube 13 are connected via a high voltage cable (not shown). The high voltage generated by the high voltage generator 17 is applied to the X-ray tube 13 via the high voltage cable. The filament heating current generated by the high voltage generator 17 is applied to the X-ray tube 13 via the high voltage cable.

A pre-collimator 19 is attached to the front of the X-ray irradiation window of the X-ray tube 13. The pre-collimator 19 limits the irradiation field of the X-rays radiated from the X-ray tube 13. More specifically, the pre-collimator 19 includes diaphragm blades made of a substance that attenuates X-rays. The irradiation field is defined by a bore formed by the diaphragm blades. The diaphragm blades can be made of any substance capable of attenuating X-rays, and is preferably made of, for example, a heavy metal such as lead.

An FOV (Field Of View) is set in the bore of the rotation frame 11. A top 21 is inserted into the bore of the rotation frame 11. The object S is placed on the top 21. The top 21 is positioned such that the imaging portion of the object S placed on the top 21 is included in the FOV. The rotation frame 11 rotates about the center axis Z at a predetermined angular velocity upon receiving power from a rotation actuator 23. As the rotation actuator 23, an arbitrary motor such as a direct drive motor or a servo motor is used. The rotation actuator 23 is stored in, for example, the gantry 10. Upon receiving a driving signal from the gantry control circuitry 25, the rotation actuator 23 generates power to rotate the rotation frame 11.

The X-ray detector 15 detects the X-rays generated by the X-ray tube 13. More specifically, the X-ray detector 15 includes a plurality of detector pixels (not shown) arranged on a two-dimensional curved surface. Each detector pixel includes a scintillator and a photoelectric conversion element. The scintillator is a substance for converting X-rays into fluorescence. As the scintillator substance, for example, NaI, BGO, or the like is used. The scintillator converts incident X-rays into a number of fluorescent photons corresponding to the intensity of the incident X-rays. The photoelectric conversion element is a circuitry element that amplifies fluorescence and converts it into an electrical signal. As the photoelectric conversion element, for example, a photomultiplier, a photodiode, or the like is used. Note that the detector pixel can be either of an indirect detection type that converts X-rays into light and then detects the light, as described above, or of a direct conversion type that directly converts X-rays into an electrical signal. As the detector pixel of the direct detection type, for example, a type including a semiconductor diode formed by attaching electrodes to two terminals of a semiconductor is applicable.

Data acquisition circuitry 27 is connected to the X-ray detector 15. The data acquisition circuitry 27 acquires, from the X-ray detector 15, data (to be referred to as raw data hereinafter) corresponding to the intensity of the X-rays detected by the X-ray detector 15 for each view. More specifically, the data acquisition circuitry 27 includes, for example, an integrated circuit (not shown) and an A/D converter (not shown) for each detector pixel. The integrated circuit integrates electrical signals from a detector pixel for each view. The A/D converter converts the integrated electrical signal from an analog signal to a digital signal (raw data). Raw data of each view is thus acquired. Raw data is a set of digital values representing the intensity of X-rays identified by the channel number and the row number of a detector pixel as a generation source and a view number representing an acquired view. The raw data is supplied to the console 50 via, for example, a noncontact data transmission unit (not shown) stored in the gantry 10. Note that another circuitry element such as a preamplifier or an IV converter may be implemented in the data acquisition circuitry 27. The data acquisition circuitry 27 includes a semiconductor integrated circuit such as an ASIC (Application Specific Integrated Circuit). The above-described circuitry elements such as the integrated circuit and the A/D converter are implemented on the semiconductor integrated circuit.

The gantry control circuitry 25 synchronously controls the high voltage generator 17, the rotation actuator 23, and the data acquisition circuitry 27, and performs X-ray CT imaging of the object S under the control of system control circuitry 61 in the console 50. The gantry control circuitry 25 includes, as hardware resources, a processing unit (processor) such as a CPU (Central Processing Unit) or an MPU (Micro Processing Unit) and a storage unit (memory) such as a ROM (Read Only Memory) or a RAM (Random Access Memory). The gantry control circuitry 25 may be provided in the gantry 10 or the console 50, or in a unit separated from the gantry 10 and the console 50. The gantry control circuitry 25 may be implemented by an ASIC (Application Specific Integrated Circuit), an FPGA (Field Programmable Logic Device), a CPLD (Complex Programmable Logic Device), or an SPLD (Simple Programmable Logic Device). The processing unit implements the function by reading out a program saved in the storage unit and executing it. Note that instead of saving the program in the storage unit, the program may directly be embedded in circuitry of the processing unit. In this case, the processing unit implements the function by reading out the program embedded in the circuitry and executing it.

As shown in FIG. 1, the console 50 includes image reconstruction circuitry 51, image processing circuitry 53, display circuitry 55, input circuitry 57, main storage circuitry 59, and the system control circuitry 61 which are connected via a bus. Data communication between the image reconstruction circuitry 51, the image processing circuitry 53, the display circuitry 55, the input circuitry 57, the main storage circuitry 59, and the system control circuitry 61 is performed via the bus.

The image reconstruction circuitry 51 reconstructs a CT image concerning the subject S based on raw data from the gantry 10. More specifically, the image reconstruction circuitry 51 includes data storage circuitry 511, a preprocessing unit 513, and a reconstruction processing unit 515. The data storage circuitry 511 is a storage unit that stores raw data transmitted from the gantry 10, such as an HDD (Hard Disk Drive), an SSD (Solid State Drive), or an integrated circuit storage unit. The preprocessing unit 513 performs preprocessing such as logarithmic transformation or metal artifact reduction processing for the raw data. The reconstruction processing unit 515 generates a CT image that expresses the spatial distribution of CT values depending on an X-ray attenuation coefficient based on the preprocessed raw data. As the image reconstruction algorithm, an existing image reconstruction algorithm, for example, an analytic image reconstruction method such as FBP (Filtered Back Projection) or CBP (Convolution Back Projection) or a statistical image reconstruction method such as ML-EM (Maximum Likelihood Expectation Maximization) or OS-EM (Ordered Subset Expectation Maximization) is used.

The image reconstruction circuitry 51 includes, as hardware resources, processing units (processors) such as a CPU or an MPU, and a GPU (Graphics Processing Unit) and storage units (memories) such as a ROM and a RAM. The image reconstruction circuitry 51 may be implemented by an ASIC, an FPGA, a CPLD, an SPLD, or the like. The processing unit implements the function of the preprocessing unit 513 and the function of the reconstruction processing unit 515 by reading out a program saved in the storage unit and executing it. Note that instead of saving the program in the storage unit, the program may directly be embedded in circuitry of the processing unit. In this case, the processing unit implements the function of the reconstruction processing unit 515 by reading out the program embedded in the circuitry and executing it. Alternatively, dedicated hardware circuitry that implements the function of the preprocessing unit 513 and dedicated hardware circuitry that implements the function of the reconstruction processing unit 515 may be implemented in the image reconstruction circuitry 51.

The image processing circuitry 53 performs various kinds of image processing for the CT image reconstructed by the image reconstruction circuitry 51. For example, if the CT image is volume data, the image processing circuitry 53 performs three-dimensional image processing such as volume rendering, surface volume rendering, image value projection processing, MPR (Multi-Planer Reconstruction) processing, and CPR (Curved MPR) processing for the CT image to generate a display image. The image processing circuitry 53 includes, as hardware resources, processing units (processors) such as a CPU or an MPU, and a GPU and storage units (memories) such as a ROM and a RAM. The image processing circuitry 53 may be implemented by an ASIC, an FPGA, a CPLD, an SPLD, or the like.

The display circuitry 55 displays various kinds of data such as a two-dimensional CT image and a display image. More specifically, the display circuitry 55 includes display interface circuitry and a display device. The display interface circuitry converts data representing a display target into a video signal. The display signal is supplied to the display device. The display device displays the video signal representing the display target. As the display device, for example, a CRT display, a liquid crystal display, an organic EL display, an LED display, a plasma display, or another arbitrary display known in the technical field can appropriately be used.

The input circuitry 57 inputs various kinds of instructions from the user. More specifically, the input circuitry 57 includes an input device and input interface circuitry. The input device accepts various kinds of instructions from the user. As the input device, a keyboard, a mouse, various kinds of switches, or the like can be used. The input interface circuitry supplies an output signal from the input device to the system control circuitry 61 via the bus. Note that the input circuitry 57 may be provided in the console 50 or the gantry 10.

The main storage circuitry 59 is a storage unit configured to store various kinds of information, such as an HDD, an SSD, or an integrated circuit storage unit. The main storage circuitry 59 may be a driving unit or the like configured to read/write various kinds of information from/to a portable storage medium such as a CD-ROM drive, a DVD drive, or a flash memory. For example, the main storage circuitry 59 stores a control program and the like concerning X-ray CT imaging according to this embodiment.

The system control circuitry 61 includes, as hardware resources, a processing unit (processor) such as a CPU or an MPU and storage units (memories) such as a ROM and a RAM. The system control circuitry 61 may be implemented by an ASIC, an FPGA, a CPLD, or an SPLD. The system control circuitry 61 functions as the core of the X-ray computed tomography imaging apparatus according to this embodiment. More specifically, the system control circuitry 61 reads out a control program stored in the main storage circuitry 59, loads it onto the memory, and controls the units of the X-ray computed tomography imaging apparatus in accordance with the loaded control program.

The image reconstruction circuitry 51, the image processing circuitry 53, and the system control circuitry 61 may be integrated on single circuitry in the console 50 or distributed to a plurality of circuitry. Alternatively, the image reconstruction circuitry 51, the image processing circuitry 53, and the system control circuitry 61 may be integrated on a single board in the console 50 or distributed to a plurality of boards.

Details of the X-ray computed tomography imaging apparatus according to this embodiment will be described below divisionally in Example 1 and Example 2.

EXAMPLE 1

FIG. 2 is a view showing the arrangement of an X-ray tube 13 and a high voltage generator 17 according to Example 1. As shown in FIG. 2, the X-ray tube 13 stores a cathode 131, an anode 133, a rotor 135, and a regulator 137. The cathode 131 is made of a metal having a thin line shape or a plate shape. When the cathode 131 has a thin line shape, the thermal response is higher than that of a plate shape, and the characteristic is empirically known well. When the cathode 131 has a plate shape, the life is longer than a thin line shape. The cathode 131 will be assumed to be a filament implemented by a metal such as tungsten or nickel having a thin line shape hereinafter. The filament 131 is connected to the high voltage generator 17 via a cable or the like. The filament 131 generates heat and emits thermoelectrons upon receiving a filament heating current supplied from the high voltage generator 17.

The anode 133 is an electrode made of a heavy metal such as tungsten or molybdenum and having a disc shape. The rotor 135 is attached to the anode 133. The anode 133 rotates as the rotor 135 rotates about its axis. The anode 133 and the rotor 135 form a rotating anode. The high voltage generator 17 applies a high voltage between the filament 131 and the anode 133. The thermoelectrons generated by the filament 131 are accelerated while being focused to a beam shape by the high voltage applied between the filament 131 and the anode 133 and collide against the anode 133 that is rotating. Upon receiving the thermoelectrons from the filament 131, the anode 133 radiates bremsstrahlung X-rays.

The regulator 137 is arranged between the filament 131 and the anode 133. The regulator 137 electrically or magnetically regulates the size of a focus on the surface of the anode 133. As the regulator 137, any hardware that electrically or magnetically biases the trajectory of the thermoelectrons is usable. For example, the regulator 137 is implemented by an electrode, a magnet, a coil, or the like. The regulator 137 will be assumed to be an electrode hereinafter. Upon receiving the voltage applied by the high voltage generator 17, the regulator 137 biases the trajectory of the thermoelectrons flying from the filament 131 to the anode 133 and regulates the size of the focus.

Under the control of gantry control circuitry 25, the high voltage generator 17 applies a high voltage and supplies a filament heating current to the X-ray tube 13. By an FSC (Focus Size Control) function, the high voltage generator 17 according to Example 1 selectively switches the size of the focus of the thermoelectrons from the cathode 131 included in the X-ray tube 13 on the anode 133 between scan and warm-up. More specifically, the high voltage generator 17 includes power supply circuitry 31, high voltage generation circuitry 33, filament heating circuitry 35, a tube voltage detector 37, a tube current detector 39, tube voltage control circuitry 41, tube current control circuitry 43, and regulator control circuitry 45.

The power supply circuitry 31 generates a direct current based on an alternating current from power supply equipment provided in the examination room or the like where a gantry 10 is placed. More specifically, the power supply circuitry 31 includes rectifying circuitry and a smoothing capacitor. The rectifying circuitry rectifies the alternating current from the power supply equipment into a direct current. The smoothing capacitor smoothes the alternating current rectified by the rectifying circuitry. An alternating current is converted into a direct current by the rectification and smoothing. Note that the power supply that supplies power to the power supply circuitry 31 is not limited to the power supply equipment and may be a capacitor or a storage battery.

The high voltage generation circuitry 33 generates a high voltage to be applied to the X-ray tube 13 under the control of the tube voltage control circuitry 41. The high voltage generation circuitry 33 and the anode 133 are connected by an anode-side high voltage cable, and the high voltage generation circuitry 33 and the filament 131 are connected by a cathode-side high voltage cable. As the high voltage generation circuitry 33, any type such as a transformer-type X-ray high voltage generator, a constant voltage-type X-ray high voltage generator, a capacitor-type X-ray high voltage generator, or an inverter-type X-ray high voltage generator is applicable. For example, the high voltage generation circuitry 33 of an inverter type includes an inverter and a high voltage transformer. The inverter switches the direct current from the power supply circuitry 31 at timing according to the control of the tube voltage control circuitry, thereby converting the direct current into an AC output pulse. The high voltage transformer converts the AC output pulse from the inverter into a DC high voltage.

The filament heating circuitry 35 generates power to heat the filament 131 under the control of the tube current control circuitry 43. As the filament heating circuitry 35, either a variable resistance type or a high-frequency heating type is applicable. For example, the filament heating circuitry 35 of a high-frequency heating type includes an inverter and a filament heating transformer. The inverter switches the direct current from the power supply circuitry 31 at timing according to the control of the tube voltage control circuitry, thereby converting the direct current into an AC output pulse. The filament heating transformer converts the AC output pulse from the inverter into a DC filament heating current.

The tube voltage detector 37 is connected between the anode-side high voltage cable and the cathode-side high voltage cable. The tube voltage detector 37 detects, as a tube voltage, a high voltage applied between the cathode 131 and the anode 133. The data of the detected tube voltage value (to be referred to as a tube voltage detection value hereinafter) is supplied to the tube voltage control circuitry 41.

The tube current detector 39 is connected to the anode-side cable. The tube current detector 39 detects, as a tube current, a current that flows to the anode-side cable due to the flow of thermoelectrons from the cathode 131 to the anode 133. The data of the detected tube current value (to be referred to as a tube current detection value hereinafter) is supplied to the tube current control circuitry 43.

The tube voltage control circuitry 41 controls the high voltage generation circuitry 33 based on comparison between a tube voltage detection value and a set tube voltage value. More specifically, the tube voltage control circuitry 41 compares the tube voltage detection value with the set tube voltage value, and feedback-controls the high voltage generation circuitry 33 such that the tube voltage detection value converges to the set tube voltage value. The data of the set tube voltage value is supplied from the gantry control circuitry 25.

The tube current control circuitry 43 controls the filament heating circuitry 35 based on comparison between a tube current detection value and a set tube current. More specifically, the tube current control circuitry 43 compares the tube current detection value with the set tube current value, and feedback-controls the filament heating circuitry 35 such that the tube current detection value converges to the set tube current value. The data of the set tube current value is supplied from the gantry control circuitry 25.

The regulator control circuitry 45 controls the regulator 137 to switch at least one of the size and position of the focus of the thermoelectrons from the filament 131 on the anode 133 between scan and warm-up. More specifically, if a signal (to be referred to as a scan signal hereinafter) representing that scan is progressing is supplied from the gantry control circuitry 25, the regulator control circuitry 45 controls the regulator 137 such that the thermoelectrons from the filament 131 focus to a focus of a size for scan. In addition, if the scan signal is supplied from the gantry control circuitry 25, the regulator control circuitry 45 may also control the regulator 137 such that the thermoelectrons from the filament 131 collide against a focus position for scan separately from or in parallel to the focus of the size. If a signal (to be referred to as a warm-up signal hereinafter) representing that warm-up is progressing is supplied from the gantry control circuitry 25, the regulator control circuitry 45 controls the regulator 137 such that the thermoelectrons focus to a focus of a size for warm-up. In addition, if the warm-up signal is supplied from the gantry control circuitry 25, the regulator control circuitry 45 may also control the regulator 137 such that the thermoelectrons from the filament 131 collide against a focus position for warm-up separately from or in parallel to the focus of the size. Note that strictly speaking, the focus position indicates the position of the center point of the focus on the anode 133.

The regulator control circuitry 45 stores a focus voltage value corresponding to the size of a focus F1 for scan and a focus voltage value corresponding to the size of a focus F2 for warm-up, which are decided in advance, in a memory or the like. In scan, if the scan signal is supplied from the gantry control circuitry 25, the regulator control circuitry 45 reads out the focus voltage value corresponding to the size of the focus F1 for scan from the memory or the like, and applies a voltage corresponding to the readout focus voltage value to the regulator 137. The focus is thus switched to the focus F1 for scan. In warm-up, if the warm-up signal is supplied from the gantry control circuitry 25, the regulator control circuitry 45 reads out the focus voltage value corresponding to the size of the focus F2 for warm-up from the memory or the like, and applies a voltage corresponding to the readout focus voltage value to the regulator 137. The focus is thus switched to the focus F2 for warm-up. That is, the regulator control circuitry 45 can move the focus to a different position with respect to the direction of the turning radius of the anode 133 between scan and warm-up.

Similarly, the regulator control circuitry 45 stores a bias voltage value corresponding to the position of the focus F1 for scan and a bias voltage value corresponding to the position of the focus F2 for warm-up, which are decided in advance, in a memory or the like. In scan, if the scan signal is supplied from the gantry control circuitry 25, the regulator control circuitry 45 reads out the bias voltage value corresponding to the position of the focus F1 for scan from the memory or the like, and applies a voltage corresponding to the readout bias voltage value to the regulator 137. The focus is thus switched to the focus F1 for scan. In warm-up, if the warm-up signal is supplied from the gantry control circuitry 25, the regulator control circuitry 45 reads out the bias voltage value corresponding to the position of the focus F2 for warm-up from the memory or the like, and applies a voltage corresponding to the readout bias voltage value to the regulator 137. The focus is thus switched to the focus F2 for warm-up. That is, the regulator control circuitry 45 can move the focus to a different position with respect to the direction of the turning radius of the anode 133 between scan and warm-up.

The tube voltage control circuitry 41, the tube current control circuitry 43, and the regulator control circuitry 45 may be implemented on a single board or implemented on a plurality of boards. Each of the tube voltage control circuitry 41, the tube current control circuitry 43, and the regulator control circuitry 45 may be implemented by analog circuitry or digital circuitry. When implemented as digital circuitry, each of the tube voltage control circuitry 41, the tube current control circuitry 43, and the regulator control circuitry 45 includes, as hardware resources, a processing unit (processor) such as a CPU or an MPU and storage units (memories) such as a ROM and a RAM. Each of the tube voltage control circuitry 41, the tube current control circuitry 43, and the regulator control circuitry 45 may be implemented by an ASIC, an FPGA, a CPLD, or an SPLD.

Figure 3:
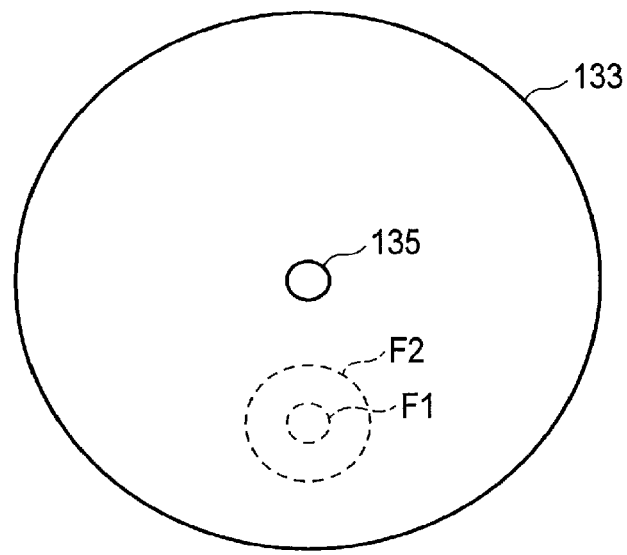
FIG. 3 is a front view of an anode on which a focus size for scan and a focus size for warm-up according to Example 1 are shown.
Figure 4:
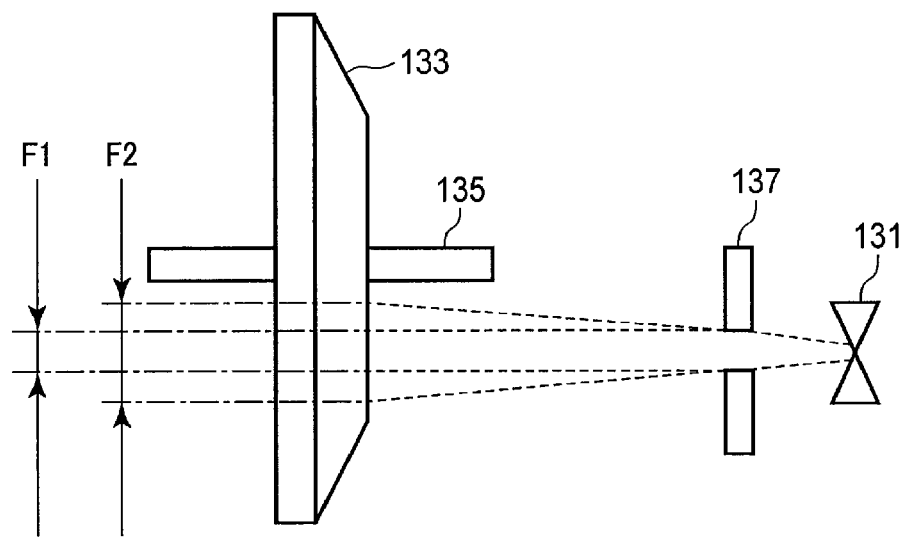
FIG. 4 is a side view of the anode on which the focus size for scan and the focus size for warm-up according to Example 1 are shown.

FIG. 3 is a front view of the anode 133 on which a focus size for scan and a focus size for warm-up are shown. FIG. 4 is a side view of the anode 133 on which the focus size for scan and the focus size for warm-up are shown. As shown in FIGS. 3 and 4, during scan, the thermoelectrons from the filament 131 focus to the focus F1 of the size for scan. During warm-up, the thermoelectrons from the filament 131 focus to the focus F2 of the size for warm-up. If the focus size for warm-up is smaller than the focus size for scan, the focus of the anode 133 may be roughened by the warm-up. The larger the focus size is, the wider the range of the anode 133 that the thermoelectrons collide against is. For this reason, if the heat amount per unit area remains unchanged, the anode 133 can be heated quickly as the focus size becomes large. Hence, to quickly heat the anode 133 while preventing focus roughness caused by warm-up, the size of the focus F2 for warm-up is set to be larger than the size of the focus F1 for scan. In addition, the size of the focus F2 for warm-up is set to a size capable of raising the temperature of the anode 133 without causing focus roughness on the anode 133.

FIG. 5 is a front view of the anode 133 on which the focus position for scan and the focus position for warm-up according to other example are shown. FIG. 6 is a side view of the anode 133 on which the focus position for scan and the focus position for warm-up according to other example are shown. As shown in FIGS. 5 and 6, during scan, the thermoelectrons from the filament 131 focus to the position of the focus F1 for scan. During warm-up, the thermoelectrons from the filament 131 focus to the position of the focus F2 for warm-up. If the position of the focus F2 for warm-up is superimposed on the position of the focus F1 for scan, the superimposed portion on the anode 133 may be roughened. Hence, the position of the focus F1 and the position of the focus F2 are set such that the position of the focus F1 for scan is not superimposed on the position of the focus F2 for warm-up. The position of the focus F1 and the position of the focus F2 are set on the same turning radius of the anode 133. To suppress wear of the portion of the anode 133 on the focus F2, the position of the focus F2 is set on the outer side of the turning radius with respect to the position of the focus F1.

An example of the operation of the X-ray computed tomography imaging apparatus according to Example 1 will be described below with reference to FIG. 7.

FIG. 7 is a timing chart of a heating current and a tube voltage concerning switching of the focus size of focus position according to Example 1. The upper graph of FIG. 7 represents the time series of the filament heating current, and the lower graph of FIG. 7 represents the time series of the tube voltage. The ordinate of the upper graph of FIG. 7 defines the filament heating current [mA], and the abscissa defines time. The ordinate of the lower graph of FIG. 7 defines the tube voltage [kV], and the abscissa defines time. Note that whether to select the focus size or focus position can arbitrarily be selected via input circuitry 57 or the like.

As shown in FIG. 7, when the user inputs a warm-up start instruction via the input circuitry 57 (t0), the gantry control circuitry 25 controls the tube voltage control circuitry 41, the tube current control circuitry 43, and the regulator control circuitry 45 to warm up the X-ray tube 13. More specifically, the gantry control circuitry 25 supplies the warm-up signal to the regulator control circuitry 45. Upon receiving the supplied warm-up signal, to change the focus size, the regulator control circuitry 45 reads out the focus voltage value corresponding to the size of the focus F2 for warm-up from the memory or the like, and applies an electric field corresponding to the readout focus voltage value to the regulator 137. To change the focus position, the regulator control circuitry 45 reads out the bias voltage value corresponding to the position of the focus F2 for warm-up from the memory or the like, and applies an electric field corresponding to the readout bias voltage value to the regulator 137. In addition, the gantry control circuitry 25 synchronously controls the tube voltage control circuitry 41 and the tube current control circuitry 43 so as to moderately raise the temperature of the anode 133 in the X-ray tube 13. To moderately raise the temperature of the anode 133 in the X-ray tube 13, the gantry control circuitry 25 controls the tube current control circuitry 43 so as to moderately raise the filament heating current value from 0 to a set tube current value A1, and controls the tube voltage control circuitry 41 so as to moderately raise the tube voltage value from 0 to a set tube voltage value V1. This enables to warm up the X-ray tube 13 by the focus F2 for warm-up. Here, "moderately" means "taking time longer than the time for the tube current detection value to reach the set tube current value A1 in a case in which the set value of feedback control by the tube current control circuitry 43 is initially set to the set tube current value A1" or "taking time longer than the time for the tube voltage detection value to reach the set tube voltage value V1 in a case in which the set value of feedback control by the tube voltage control circuitry 41 is initially set to the set tube voltage value V1".

For example, from start time t0 to end time t1 of warm-up, the tube current control circuitry 43 may linearly raise the feedback control set value from the initial value to the set tube current value A1, and similarly, the tube voltage control circuitry 41 may linearly raise the feedback control set value from the initial value to the set tube voltage value V1. The warm-up period is preferably set in advance via the input circuitry 57 or the like. Alternatively, the tube current control circuitry 43 and the tube voltage control circuitry 41 may end the warm-up when the heat amount applied to the X-ray tube 13 reaches a predetermined threshold. The heat amount applied to the X-ray tube 13 may be, for example, calculated based on the tube voltage detection value from the tube voltage detector 37 and the tube current detection value from the tube current detector 39 or measured by a calorimeter provided on the X-ray tube 13.

The manner the feedback control set value rises is not limited to the linear rise. For example, the tube voltage control circuitry 41 may increase the feedback control set value stepwise from the initial value to the set tube voltage value V1, and the tube current control circuitry 43 may increase the feedback control set value stepwise from the initial value to the set tube current value A1 to moderately raise the temperature of the anode 133 in the X-ray tube 13. More specifically, the tube voltage control circuitry 41 waits for the elapse of set time in each feedback control set value from the initial set value to the set tube voltage value V1. Every time the set time elapses, the tube voltage control circuitry 41 increases the feedback control set value by one step. When the set time elapses in a case in which the set tube voltage value V1 is set to the feedback control set value, the tube voltage control circuitry 41 stops the high voltage generation circuitry 33. Similarly, the tube current control circuitry 43 waits for the elapse of set time in each feedback control set value from the initial set value to the set tube current value A1. Every time the set time elapses, the tube current control circuitry 43 increases the feedback control set value by one step. When the set time elapses in a case in which the set tube current value A1 is set to the feedback control set value, the tube current control circuitry 43 stops the filament heating circuitry 35.

In the above explanation, the feedback control set value is increased every time the set time elapses. However, the embodiment is not limited to this. For example, the tube voltage control circuitry 41 and the tube current control circuitry 43 may monitor the heat amount applied to the X-ray tube 13 in each feedback control set value, and increase the feedback control set value when the heat amount exceeds a threshold.

The timings of increasing the feedback control set values of the heating current and the tube voltage are not particularly limited. That is, in this embodiment, the feedback control set values of the heating current and the tube voltage may be increased at the same timing or increased alternately. When the feedback control set values are increased alternately, the temperature of the X-ray tube 13 can be raised more moderately, and an abrupt increase in the temperature can be prevented.

The regulator control circuitry 45 may control the regulator 137 and vibrate the focus position for warm-up with respect to the radial direction of the anode 133. When the focus position for warm-up is vibrated with respect to the radial direction of the anode 133, the thermoelectrons collide against a wide range of the anode 133, and the anode 133 can be heated more quickly.

At the time of warm-up as well, X-rays are generated by the collision of the thermoelectrons against the anode 133. For this reason, the diaphragm blades of a pre-collimator 19 are preferably closed at the time of warm-up. When the diaphragm blades are closed, it is possible to prevent outside leakage of the X-rays generated by the anode 133, degradation of the X-ray detector 15, and unnecessary exposure of a medical worker such as a user and an object such as a patient.

When high voltage generation by the high voltage generation circuitry 33 and heating power generation by the filament heating circuitry 35 end, the warm-up ends (t1). The warm-up is performed typically for about 5 min. In case of emergency, the warm-up is performed for about 1 to 2 min. When the warm-up ends, the object is positioned. High voltage application and heating current supply stop during the time from the end of warm-up (time t1) to the start of scan (time t2).

When the user inputs a scan start instruction via the input circuitry 57 (t2), the gantry control circuitry 25 controls the high voltage generator 17, a rotation actuator 23, and data acquisition circuitry 27 to start scan. At this time, the gantry control circuitry 25 supplies the scan signal to the regulator control circuitry 45. Upon receiving the supplied scan signal, to change the focus size, the regulator control circuitry 45 reads out the focus voltage value corresponding to the size of the focus F1 for scan from the memory or the like, and controls the regulator 137 to apply an electric field corresponding to the readout focus voltage value. The size of the focus of the thermoelectrons is thus switched to the size of the focus F1 for scan. To change the focus position, the regulator control circuitry 45 reads out the bias voltage value corresponding to the position of the focus F1 for scan from the memory or the like, and applies an electric field corresponding to the readout bias voltage value to the regulator 137. The position of the focus of the thermoelectrons is thus switched to the position of the focus F1 for scan.

The gantry control circuitry 25 controls the rotation actuator 23 to rotate the rotation frame. When the angular velocity of the rotation frame reaches a set value, the gantry control circuitry 25 controls the high voltage generator 17 and the data acquisition circuitry 27 and repeats X-ray exposure and data acquisition. At this time, the gantry control circuitry 25 controls the tube voltage control circuitry 41 such that the high voltage generation circuitry 33 applies a high voltage corresponding to the set tube voltage value V1 to the X-ray tube 13, and controls the tube current control circuitry 43 such that the filament heating circuitry 35 supplies a heating current corresponding to the set tube current value A1 to the filament 131. X-ray exposure is performed by the high voltage application and the heating current supply. In this embodiment, warm-up is performed before scan. Hence, even if the high voltage corresponding to the set tube voltage value V1 is applied to the X-ray tube 13, and the heating current of the set tube current value A1 is supplied to the X-ray tube 13 immediately after the start of the scan, the X-ray tube 13 can continuously generate X-rays for exposure without discharge.

The X-rays generated by the X-ray tube 13 for exposure pass through the object and are detected by an X-ray detector 15. The data acquisition circuitry 27 acquires, for each view, raw data according to the intensity of the X-rays detected by the X-ray detector 15. The acquired raw data is transmitted to a console 50. Image reconstruction circuitry 51 reconstructs a CT image concerning the object based on the raw data from the gantry 10. The reconstructed CT image is displayed by display circuitry 55.

When a predetermined time elapses (t3), the gantry control circuitry 25 controls the high voltage generator 17, the rotation actuator 23, and the data acquisition circuitry 27 to end the scan.

The explanation of the example of the operation of the X-ray computed tomography imaging apparatus according to Example 1 will be ended.

Note that in the above description, in warm-up, the heating current value is raised to the set value A1, and the tube voltage value is raised to the set value V1. However, the embodiment is not limited to this. For example, in warm-up, the heating current value need not be raised to the set value A1 or may be raised to a value larger than the set value A1. Similarly, in warm-up, the tube voltage value need not be raised to the set value V1 or may be raised to a value larger than the set value V1.

In the above description, one focus size for scan is assumed to exist. However, the embodiment is not limited to this. For example, a plurality of focus sizes for scan may be set. For example, as the focuses for scan, a large focus having a relatively large size and a small focus having a relatively small size may be set. In this case as well, the size of the focus for warm-up is set to be larger than the size of the large focus for scan.

In the above description, at least one of the focus size and the focus position is switched. However, both of the focus size and the focus position may be switched.

As described above, the X-ray computed tomography imaging apparatus according to Example 1 selectively switches at least one of the focus size and the focus position between scan and warm-up by the focus size and focus position changing function. If the focus size and the focus position in warm-up are different from the focus size and the focus position in scan, the roughness of the surface of the anode 133 can be reduced as compared to a case in which the focus size and the focus position in scan are the same as those in warm-up. In addition, warm-up can be performed more efficiently by setting a focus size and a focus position specialized to warm-up. Furthermore, since the number of filaments 131 can be decreased as compared to Example 2 to be described later, the circuit scale or cost according to an increase in the number of filaments 131 can be reduced.

Hence, according to this embodiment, it is possible to suppress degradation of the X-ray tube caused by warm-up.

EXAMPLE 2

In Example 1, the regulator 137 switches between the focus size and the focus position for scan and the focus size and the focus position for warm-up. In Example 2, an X-ray tube 13 is assumed to store a filament for scan and a filament for warm-up. An X-ray computed tomography imaging apparatus according to Example 2 will be described below. Note that the same reference numerals as in Example 1 denote the same constituent elements in the following explanation, and a repetitive description will be made only when necessary.

Figure 8:
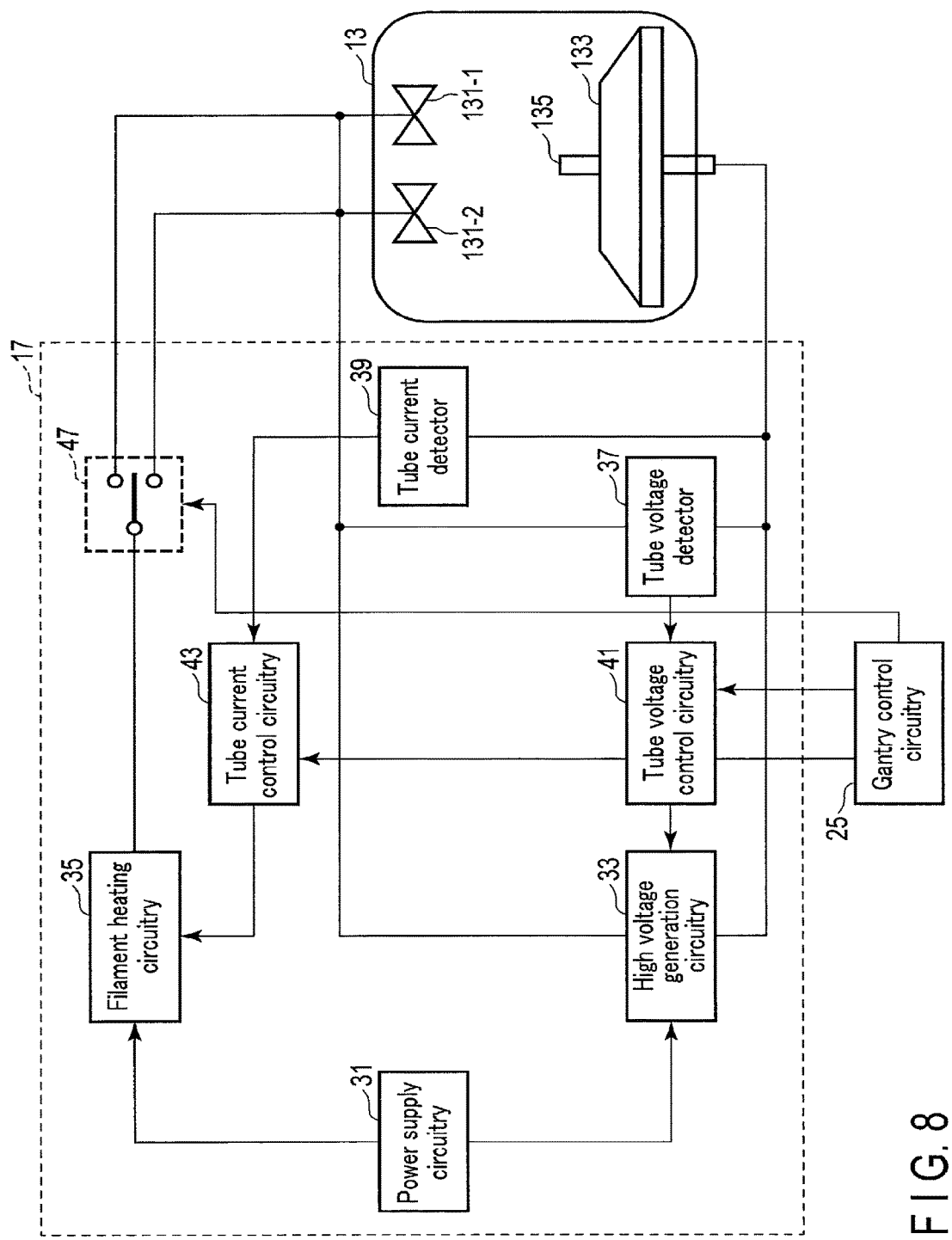
FIG. 8 is a view showing the arrangement of an X-ray tube and a high voltage generator according to Example 2.

FIG. 8 is a view showing the arrangement of the X-ray tube 13 and a high voltage generator 17 according to Example 2. As shown in FIG. 8, the X-ray tube 13 according to Example 2 includes a filament 131-1 for scan and a filament 131-2 for warm-up. The filament 131-1 for scan has a form capable of forming a focus size for scan, and the filament 131-2 for warm-up has a form capable of forming a focus size for warm-up. As in Example 1, the focus size for warm-up is set to be larger than the focus size for scan.

The high voltage generator 17 according to Example 2 includes power supply circuitry 31, high voltage generation circuitry 33, filament heating circuitry 35, a tube voltage detector 37, a tube current detector 39, tube voltage control circuitry 41, tube current control circuitry 43, and a switch 47. The switch 47 connects the filament heating circuitry 35 switchably between the filament 131-1 for scan and the filament 131-2 for warm-up. The switch 47 selectively connects the filament heating circuitry 35 to the filament 131-1 for scan or the filament 131-2 for warm-up under the control of gantry control circuitry 25. More specifically, when the scan signal is supplied from the gantry control circuitry 25, the switch 47 connects the filament heating circuitry 35 to the filament 131-1 for scan. When the warm-up signal is supplied from the gantry control circuitry 25, the switch 47 connects the filament heating circuitry 35 to the filament 131-2 for warm-up.

Figure 9:
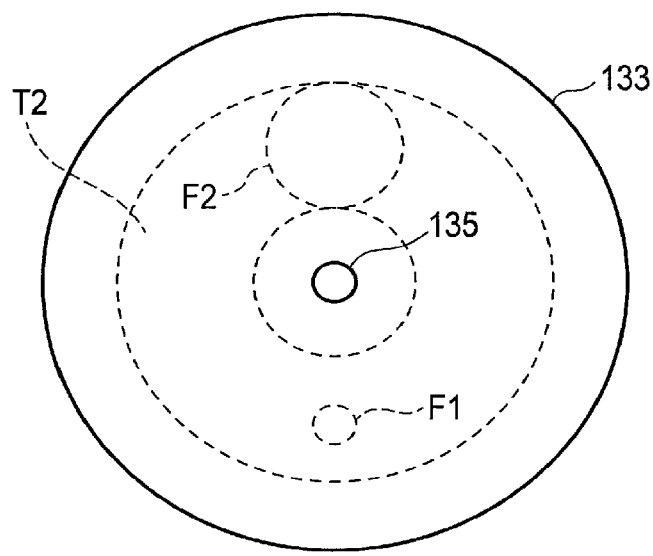
FIG. 9 is a front view of an anode on which a focus size for scan and a focus size for warm-up according to Example 2 are shown.
Figure 10:
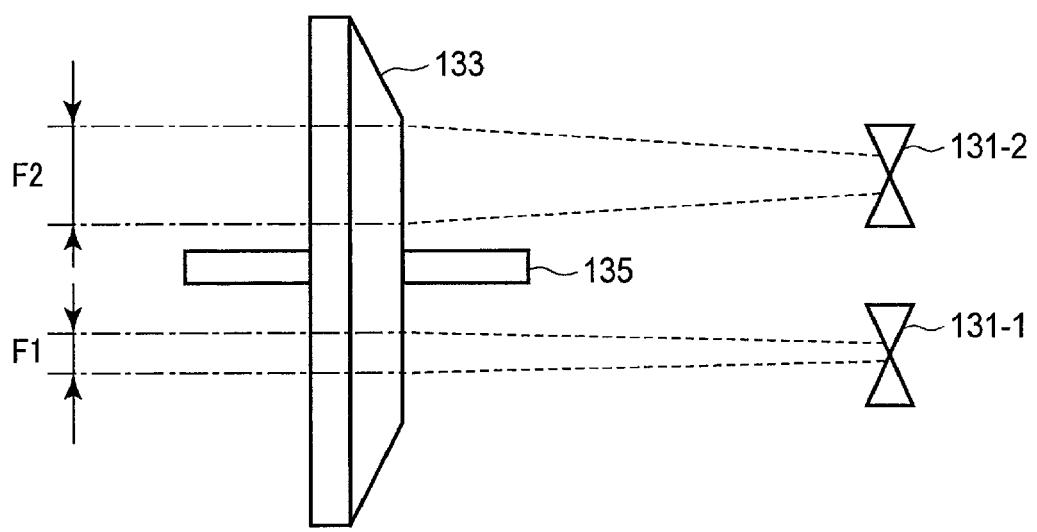
FIG. 10 is a side view of the anode on which the focus size for scan and the focus size for warm-up according to Example 2 are shown.

FIG. 9 is a front view of the anode 133 on which a focus size for scan and a focus size for warm-up according to Example 2 are shown. FIG. 10 is a side view of the anode 133 on which the focus size for scan and the focus size for warm-up according to Example 2 are shown. As shown in FIGS. 9 and 10, thermoelectrons from the filament 131-1 for scan focus to the focus F1 of the size for scan. Thermoelectrons from the filament 131-2 for warm-up focus to the focus F2 of the size for warm-up. To heat a wide range of the anode 133, the size of the focus F2 for warm-up is set to be larger than the size of the focus F1 for scan. In addition, the size of the focus F2 for warm-up is set to a size capable of raising the temperature of the anode 133. For this reason, the filament 131-2 for warm-up is preferably designed to a size larger than the size of the filament 131-1 for scan.

The filament 131-1 for scan and the filament 131-2 for warm-up are arranged such that the focus F1 for scan on the anode 133 is included in a trajectory T2 of the focus F2 for warm-up. When the focus F1 for scan is included in the trajectory T2 of the focus F2 for warm-up, a portion of the anode 133 to be used for scan can reliably be heated in warm-up.

Recoil electrons fly from the anode 133 due to the collision of the thermoelectrons or X-ray radiation from the anode 133. If the filament 131-1 or 131-2 is arranged at a position close to the anode 133, the recoil electrons may collide against the filament 131-1 or 131-2 and degrade the filament 131-1 or 131-2. Hence, the filaments 131-1 and 131-2 are preferably arranged at positions not to be influenced by the recoil electrons flying from the anode 133. For example, the filaments 131-1 and 131-2 are preferably arranged at positions apart from the anode 133 so the recoil electrons flying from the anode 133 do not collide.

The distance between the filament 131-1 and the anode 133 and the distance between the filament 131-2 and the anode 133 can arbitrarily be designed in accordance with the size of the focus F1 for scan and the size of the focus F2 for warm-up. At this time, the distance between the filament 131-1 and the anode 133 and the distance between the filament 131-2 and the anode 133 may be the same or different.

An example of the operation of the X-ray computed tomography imaging apparatus according to Example 2 will be described below with reference to FIG. 11.

Figure 11:
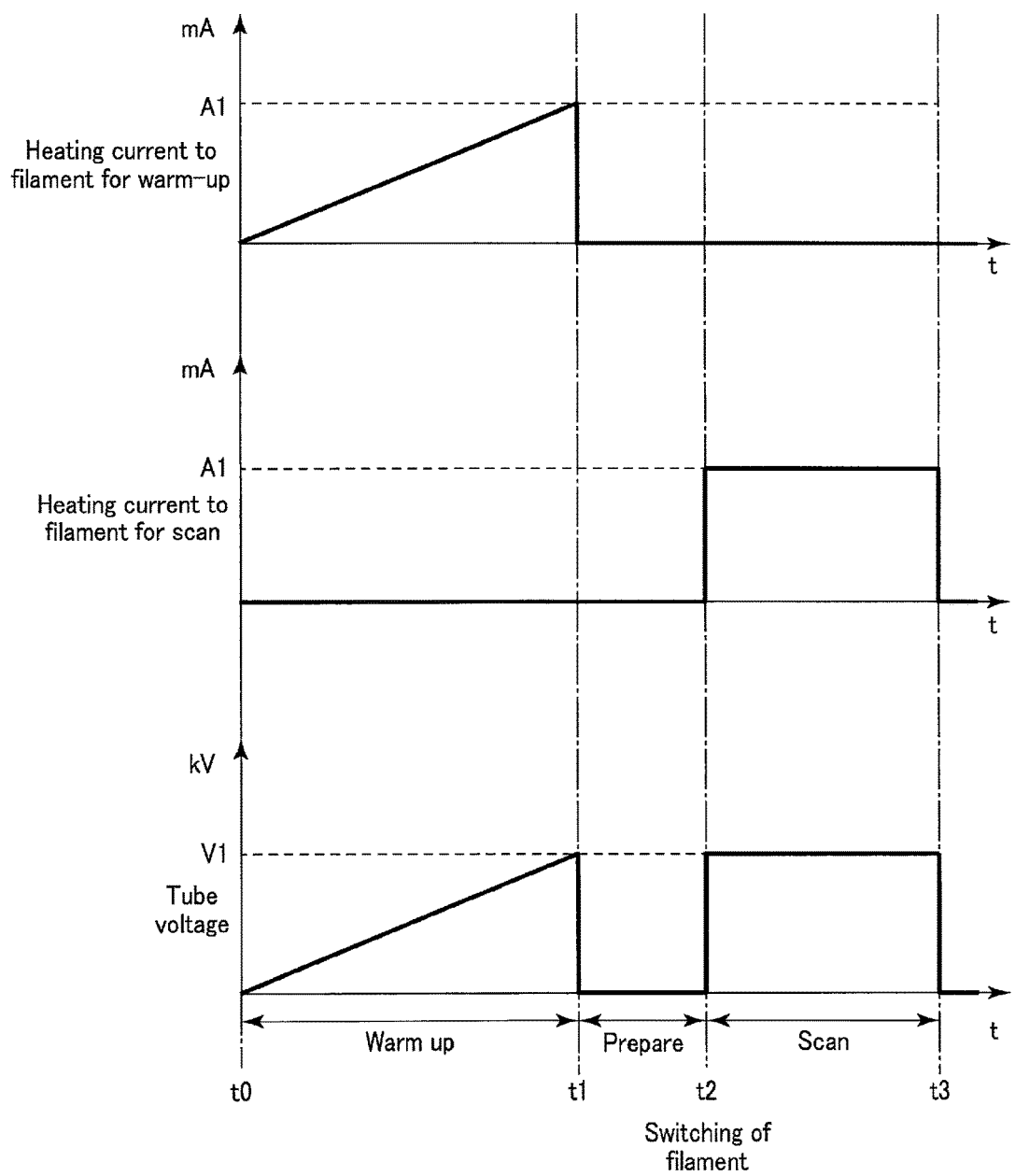
FIG. 11 is a timing chart of a heating current and a tube voltage concerning switching of a filament according to Example 2.

FIG. 11 is a timing chart of a heating current and a tube voltage concerning switching between the filament 131-1 for scan and the filament 131-2 for warm-up according to Example 2. The upper graph of FIG. 11 represents the time series of a heating current to the filament 131-2 for warm-up, the middle graph of FIG. 11 represents the time series of a heating current to the filament 131-1 for scan, and the lower graph of FIG. 11 represents the time series of the tube voltage. The ordinate of the upper and middle graphs of FIG. 11 defines the filament heating current [mA], and the abscissa defines time. The ordinate of the lower graph of FIG. 11 defines the tube voltage [kV], and the abscissa defines time.

As shown in FIG. 11, when the user inputs a warm-up start instruction via input circuitry 57 (t0), the gantry control circuitry 25 controls the tube voltage control circuitry 41, the tube current control circuitry 43, and the switch 47 to warm up the X-ray tube 13. More specifically, the gantry control circuitry 25 supplies the warm-up signal to the switch 47. Upon receiving the supplied warm-up signal, the switch 47 connects the filament heating circuitry 35 to the filament 131-2 for warm-up. In addition, the gantry control circuitry 25 synchronously controls the tube voltage control circuitry 41 and the tube current control circuitry 43 so as to moderately raise the temperature of the anode 133 in the X-ray tube 13. It is therefore possible to warm up the X-ray tube 13 using the filament 131-2 for warm-up and suppress wear of the filament 131-1 for scan that occurs when the filament is used for both warm-up and scan. Note that the control form of the heating current and the tube voltage in the warm-up is the same as in Example 1, and a description thereof will be omitted.

When high voltage generation by the high voltage generation circuitry 33 and heating power generation by the filament heating circuitry 35 end, the warm-up ends (t1). When the warm-up ends, the object is positioned.

When the user inputs a scan start instruction via the input circuitry 57 (t2), the gantry control circuitry 25 controls the high voltage generator 17, a rotation actuator 23, and data acquisition circuitry 27 to start scan. At this time, the gantry control circuitry 25 supplies the scan signal to the switch 47. Upon receiving the supplied scan signal, the switch 47 connects the filament heating circuitry 35 to the filament 131-1 for scan. At this time, the gantry control circuitry 25 controls the rotation actuator 23 to rotate the rotation frame. When the angular velocity of the rotation frame reaches a set value, the gantry control circuitry 25 controls the high voltage generator 17 and the data acquisition circuitry 27 and repeats X-ray exposure and data acquisition. At this time, the gantry control circuitry 25 controls the tube voltage control circuitry 41 such that the high voltage generation circuitry 33 applies a high voltage corresponding to set tube voltage value V1 to the X-ray tube 13, and controls the tube current control circuitry 43 such that the filament heating circuitry 35 supplies a heating current corresponding to a set tube current value A1 to the filament 131. In this embodiment, warm-up is performed before scan. Hence, even if the high voltage corresponding to the set tube voltage value V1 is applied to the X-ray tube 13, and the heating current of the set tube current value A1 is supplied to the X-ray tube 13 immediately after the start of the scan, the X-ray tube 13 can continuously generate X-rays for exposure without discharge.

The X-rays generated by the X-ray tube 13 for exposure pass through the object and are detected by an X-ray detector 15. The data acquisition circuitry 27 acquires, for each view, raw data according to the intensity of the X-rays detected by the X-ray detector 15. The acquired raw data is transmitted to a console 50. Image reconstruction circuitry 51 reconstructs a CT image concerning the object based on the raw data from the gantry 10. The reconstructed CT image is displayed by a display circuitry 55.

When a predetermined time elapses (t3), the gantry control circuitry 25 controls the high voltage generator 17, the rotation actuator 23, and the data acquisition circuitry 27 to end the scan.

The explanation of the example of the operation of the X-ray computed tomography imaging apparatus according to Example 2 will be ended.

Note that in the above description, the X-ray computed tomography imaging apparatus according to Example 2 does not include the regulator 137 and the regulator control circuitry 45. However, Example 2 is not limited to this. That is, the X-ray tube 13 according to Example 2 may include the regulator 137, and the high voltage generator 17 may include the regulator control circuitry 45. In this case, in warm-up, the regulator control circuitry 45 may control the regulator 137 and vibrate the focus position on the anode 133 by the thermoelectrons from the filament 131-2 for warm-up with respect to the radial direction of the anode 133. When the focus position is vibrated with respect to the radial direction of the anode 133, the thermoelectrons collide against a wide range of the anode 133, and the anode 133 can be heated more quickly.

In the above description, one filament 131-1 for scan is assumed to exist. However, the embodiment is not limited to this. For example, a plurality of filaments 131-1 for scan may be provided. For example, as the filaments 131-1 for scan, a large focus filament having a relatively large focus size and a small focus filament having a relatively small focus size may be provided. In this case as well, the focus size of the filament 131-2 for warm-up is set to be larger than the focus size of the large focus filament for scan.

As described above, the X-ray computed tomography imaging apparatus according to Example 2 includes the X-ray tube 13 with the filament 131-1 for scan and the filament 131-2 for warm-up. When different filaments are used in scan and warm-up, warm-up can be performed without an influence on the life of the filament 131-1 for scan or the like. It is therefore possible to reduce wear of the filament 131-1 for scan. When the size of the filament 131-2 for warm-up is optimized, unwanted degradation of the anode 133 can be prevented. When a filament of a size specialized to warm-up is provided, warm-up can be performed more efficiently. In addition, control for changing the focus size can be omitted as compared to Example 1 described above.

Hence, according to this embodiment, it is possible to suppress degradation of the X-ray tube caused by warm-up.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography imaging apparatus comprising:
   an X-ray tube including a cathode configured to generate thermoelectrons, an anode configured to generate X-rays upon receiving the thermoelectrons from the cathode, and a regulator configured to apply an electric field or a magnetic field to focus or bias the thermoelectrons from the cathode;
   an X-ray detector configured to detect the X-rays generated by the anode;

data acquisition circuitry configured to acquire data corresponding to the X-rays detected by the X-ray detector;

image generation circuitry configured to generate an image based on the acquired data;

a blocking member configured to retractably block an X-ray path from the X-ray tube to the X-ray detector; and control circuitry configured to control the regulator to switch at least one of a size and a position of a focus of the thermoelectrons from the cathode on the anode between scan and warm-up, wherein the control circuitry controls the blocking member to block the X-ray path during the warm-up, and to allow the X-rays to traverse the X-ray path during the scan.

2. The apparatus of claim 1, wherein the control circuitry controls the regulator to set the size of the focus on the anode to a first size in the scan and set the size of the focus on the anode to a second size larger than the first size in the warm-up.

3. The apparatus of claim 2, wherein the control circuitry controls the regulator to set the size of the focus to the second size according to a start of the warm-up and set the size of the focus to the first size according to a start of the scan.

4. The apparatus of claim 1, wherein in the warm-up, the control circuitry controls the regulator to vibrate a position of the focus of the thermoelectrons from the cathode on the anode with respect to a direction of a turning radius of the anode.

5. The apparatus of claim 1, wherein in the warm-up, the control circuitry controls the regulator to move a position of the focus of the thermoelectrons from the cathode on the anode to a position different from that in the scan with respect to a direction of a turning radius of the anode.

6. An X-ray computed tomography imaging apparatus comprising:

an X-ray tube including a first cathode used for scan and configured to generate thermoelectrons, a second cathode used for warm-up and configured to generate thermoelectrons, and an anode configured to generate X-rays upon receiving the thermoelectrons from the first cathode or the second cathode;

an X-ray detector configured to detect the X-rays generated by the anode;

control circuitry configured to control, when transitioning from the warm-up to the scan, the X-ray tube to switch from the second cathode, which is used during the warmup, to the first cathode, which is used during the scan;

data acquisition circuitry configured to acquire data corresponding to the X-rays detected by the X-ray detector; and image generation circuitry configured to generate an image based on the acquired data.

7. The apparatus of claim 6, further comprising:

a switch configured to switch a supply destination of a current between the first cathode and the second cathode; and control circuitry configured to control the switch to supply the current to the first cathode in the scan and supply the current to the second cathode in the warm-up.

8. The apparatus of claim 7, wherein the control circuitry controls the switch to supply the current to the second cathode according to a start of the warm-up, controls the switch not to supply the current to the second cathode according to an end of the warm-up, and controls the switch to supply the current to the first cathode according to a start of the scan.

9. The apparatus of claim 6, wherein the first cathode and the second cathode are arranged such that a focus of the thermoelectrons from the first cathode on the anode is included in a second trajectory of the focus of the thermoelectrons from the second cathode.

10. The apparatus of claim 6, wherein the second cathode is arranged at a position not to be influenced by recoil electrons generated according to a collision of the thermoelectrons against the anode.

11. The apparatus of claim 6, wherein the second cathode contains a metal having a thin line shape or a plate shape.

12. The apparatus of claim 6, further comprising a regulator configured to apply an electric field or a magnetic field to focus the thermoelectrons from the first cathode or the second cathode, wherein the control circuitry controls the regulator to vibrate a position of a focus of the thermoelectrons from the second cathode on the anode in the warm-up with respect to a direction of a turning radius of the anode.

* * * * *